(12) United States Patent
Pedrizzetti et al.

(10) Patent No.: US 8,029,444 B2
(45) Date of Patent: Oct. 4, 2011

(54) METHOD FOR ESTIMATING TISSUE VELOCITY VECTORS AND TISSUE DEFORMATION FROM ULTRASONIC DIAGNOSTIC IMAGING DATA

(75) Inventors: Gianni Pedrizzetti, Prato (IT); Giovanni Tonti, Sulmona (IT)

(73) Assignees: Esoate S.p.A., Casale Monferrato (IT); Amid Srl, Rome (IT)

( * ) Notice: Subject to any disclaimer, the term of this patent is extended or adjusted under 35 U.S.C. 154(b) by 257 days.

(21) Appl. No.: 10/957,150

(22) Filed: Sep. 30, 2004

(65) Prior Publication Data

US 2005/0070798 A1 Mar. 31, 2005

(30) Foreign Application Priority Data

Sep. 30, 2003 (EP) .................................... 03425638

(51) Int. Cl.
*A61B 8/00* (2006.01)
(52) U.S. Cl. ........ 600/438; 382/128; 600/441; 600/443; 600/447
(58) Field of Classification Search .................. 382/128; 600/441, 443, 447, 438
See application file for complete search history.

(56) References Cited

U.S. PATENT DOCUMENTS

| | | | |
|---|---|---|---|
| 6,270,459 B1 * | 8/2001 | Konofagou et al. | 600/449 |
| 6,508,768 B1 * | 1/2003 | Hall et al. | 600/443 |
| 6,674,879 B1 * | 1/2004 | Weisman et al. | 382/128 |
| 6,944,551 B2 * | 9/2005 | Chen et al. | 702/49 |
| 2002/0072674 A1 * | 6/2002 | Criton et al. | 600/454 |
| 2003/0083578 A1 * | 5/2003 | Abe et al. | 600/447 |

OTHER PUBLICATIONS

B.A. Lin, S. Einav, and M. Gharib, "Digital Ultrasound Speckle Image Velocimetry for Quantitative Cardiovascular Flow Visualization", 2003 Summer Bioengineering Conference; Jun. 25-29, 2003; Sonesta Beach Resort, Key Biscayne, Fla.*
E. Trahey, S. M. Hubbard, and O. T. Von Ramm, "Angle independent blood flow detection by frame-to-frame correlation of B-mode images," Ultrasonics 26: 271-276, 1988.*

* cited by examiner

*Primary Examiner* — Long V. Le
*Assistant Examiner* — Ellsworth Weatherby
(74) *Attorney, Agent, or Firm* — Woodard Emhardt Moriarty McNett & Henry LLP

(57) ABSTRACT

A method is disclosed for estimating tissue velocity vectors and oriented strain from ultrasonic diagnostic imaging data. Reference points are defined from evaluation of image data derived from reflected ultrasonic beams in order to determine the direction of motion and the velocity vector of the reference points. The velocity of motion for corresponding reference points between two successive image frames is determined by applying a particle image velocimetry technique. Components of the tissue strain is then obtained from time integration of the strain-rate that is determined from the gradient of velocity estimated from the velocity data in two or more reference points.

8 Claims, No Drawings

METHOD FOR ESTIMATING TISSUE VELOCITY VECTORS AND TISSUE DEFORMATION FROM ULTRASONIC DIAGNOSTIC IMAGING DATA

CROSS REFERENCE TO RELATED APPLICATION

The present application claims the benefit of European Patent Application Serial No. 03425638.8, filed on Sep. 30, 2003, which is hereby incorporated by reference in its entirety.

FIELD OF THE INVENTION

This invention relates to a method for estimating tissue velocity vectors and tissue deformation, such as oriented strain and shear, from ultrasonic diagnostic imaging data.

BACKGROUND

In many diagnostic evaluations of ultrasound images, the quantitative evaluation of the tissue kinematic properties (velocity and deformation) improves the ability to identify dysfunctions. A field where this kind of analysis has a particular relevance is the field of echocardiographic diagnostic imaging. In this field, the assessment of the effective ventricular function requires the knowledge of numerous properties about the ventricular dynamics.

A recent technique for evaluating velocity is Doppler Tissue Imaging, or DTI. This technique allows the measurement of tissue velocity over all points in the ventricular wall. The measurement of velocity itself provides direct information about the wall motion and helps to uncover abnormalities not immediately observable from tissue visualisation in B-mode imaging. The velocity measurement contains information about rigid body displacement and contraction/distension, the latter being immediately related to myocardial activity. Post processing of the DTI velocity data allows evaluation of additional quantities, namely, strain-rate and strain, that are strictly related to the regional function. Segmental strain gives a direct evaluation of the degree of contractility of the myocardium during systole, as well as of its relaxation during ventricular filling.

Nevertheless, DTI suffers from a few drawbacks consisting in limitations of the technique. The evaluation of velocity, particularly when strain rate and strain are evaluated, requires a higher frame rate with respect to B-mode imaging because velocity is a more rapidly varying function than B-mode displacement. A Doppler signal requires additional processing with respect to a simple echo.

Doppler tissue imaging suffers a further intrinsic limitation due to the fact that only the component of velocity along a scanline can be measured. This limitation has several drawbacks. When tissue moves in a direction that is not aligned with the scanline, the Doppler velocity does not reflect the effective tissue kinematics. Only the component of strain and strain-rate along the scanline can be evaluated, giving a reduced view of the local deformation state. This limits the application of DTI to the anatomic sites that can be imaged aligned along a scanline. In echocardiography this corresponds essentially to the interventricular septum and to the lateral walls in apical view.

A strain rate analysis method in ultrasonic diagnostic imaging applying the above mentioned DTI technique is disclosed in WO 02/45587. According to this document, strain-rate analysis is performed for ultrasonic images in which the spatial gradient of velocity is calculated in the direction of tissue motion. Strain-rate is calculated for cardiac ultrasound images in the direction of motion which, for myocardial images, may be either in the plane of the myocardium or across the myocardium. Strain-rate information is calculated for a sequence of images of a heart cycle and displayed for an automatically drawn border such as the endocardial border over the full heart cycle. Using DTI techniques, the method of document WO02/45587 suffers the same drawbacks as the DTI technique. Furthermore WO02/45587 teaches how to carry out the automatic drawing of a border and the successive tracking of that border during its motion. In any case such a method is affected, as are all the other border detection methods that are based on arbitrary definitions of a border, by non complete reliability and thus see rare practical use in clinic diagnosis, since the imaged structures are often not so easy to be determined.

From the fluid dynamics perspective, a velocity field estimation method exists that is known as called Particle Image Velocimetry, or PIV. According to this method, a sequence of grey scale images are taken on an illuminated slice of a fluid seeded with non buoyant micro particles in order to measure the velocity of the micro-particles from the sequence of images. This method is an optical flow method and, as such, it is based on the assumption of conservation of brightness. According to this assumption, an object (i.e., a patch of brightness) displaces without local changes from one image frame to the consecutive frame. PIV is actually well suited for fluid motion where relevant deformations are present and it has been widely employed in measuring turbulent flow and shows good reliability in such extreme conditions when the explicit subject is not clearly identifiable. For better understanding of PIV, see Adrian R J, Particle-Image technique for experimental fluid mechanics, Annu. Rev. Fluid Mech. 1991; 23, 261; Melling A, Tracer particles and seeding for particle image velocimetry, Meas. Sci. Technol. 1997; 8, 1406; Singh A. Optic Flow Computation: A unified Perspective, Piscataway, N.J.; IEEE Comput. Soc. Press, 1992; Barrow J L, Fleet D J, Beuchermin S., Performance of optical flow techniques, International Journal of Computer Vision 1994; 12, 43-77; Hu H. Saga, T. Kobayashi, T. Taniguchi, N., Research on the vertical and turbulent structures in the lobed jet flow by using LIEF and PIV, Meas. Sci. Technolo. 2000; 1, 698 and Browne P, Ramuzat A, Saxena R, Yoganathan A P.

The present invention aims to provide a method for estimating tissue velocity vectors and deformation state, such as, for example, strain and shear, from ultrasonic diagnostic imaging data which does not need to acquire ultrasonic image data in Doppler mode and which can obviate the drawbacks of the velocity and strain evaluation carried out starting from the said Doppler mode ultrasonic data, while still furnishing a reliable and precise evaluation of the velocity vector and deformation tensor.

Furthermore the present invention aims to provide an evaluation of velocity vectors and strain data which allows the determination of velocity components which are transversal to the scanline, and all of the independent components of a two dimensional strain consisting of the longitudinal strain along two orthogonal axis, particularly along the tissue and across the thickness, and in the shear.

SUMMARY OF THE INVENTION

It is an object of the present invention to estimate estimating tissue velocity vectors and deformation from ultrasonic diagnostic imaging data. Ultrasonic imaging data is acquired from an object by transmitting ultrasound beams against the object and receiving the corresponding reflected beams. Reference points are defined in an ultrasonic image field that corresponds to the ultrasonic image data obtained from an evaluation of the reflected beams and the direction of motion and the velocity vector of the reference points are determined from the ultrasonic image data. The ultrasound imaging data consist of a sequence of at least two image frames, the imaging data are B-mode grey-scale echographic images and the velocity of motion of each reference point between two successive B-mode image frames is determined by applying an optical flow method, such as a particle image velocimetry technique.

DESCRIPTION OF THE EMBODIMENTS

The particle image velocimetry techniques applied in the present invention are described as follows. At least two consecutive B-mode and grey scale image frames along an ultrasound scanline are acquired, and at least one identical point in those two consecutive image frames is defined. A small region of N×N pixels, where N=natural number, is defined in each frame and is centered on that point. A first displacement and velocity estimation cycle is made of that point between the two consecutive frames by calculating the cross-correlation between the two small regions of pixels. The position where the local correlation of the two consecutive frames is at a maximum is then determined, as well as the displacement of that maximum from the first frame to the second frame. The displacement is defined as the displacement of the point from its position in the first frame to its position in the second frame of the said two consecutive frames. Calculations determine the velocity as being the quotient of the displacement of the point from its position in the first of the two consecutive frames to its position in the second of the said two consecutive frames, and the time distance between the said two consecutive frames. The deformation from time integration of the appropriate component of the velocity gradient is evaluated by estimating the spatial derivatives from velocity in two or more points.

In a further embodiment, a sequence of more than two consecutive frames are acquired and the displacement of a certain defined point and the velocity is evaluated as described before for each couple of consecutive frames in the sequence of consecutive frames.

According to still another embodiment, more than one point is defined and the described method steps are applied to each one of the points.

Considering a local region of image frames acquired from N×N pixels for a certain point X centered in the region of the first of the consecutive frames of a sequence of frames, the above disclosed first estimation cycle would lead to the determination of a sequence of displacements $\Delta x_i$ for the point X from a frame i to the following frame i+1. The velocity of the point X in the displacement from the frame i to the following consecutive frame i+1 of the sequence of frames is then $\Delta x_i/\Delta t_i$, which is the time interval between the two consecutive frames i and i+1. If necessary, the above mentioned estimation cycle steps may be followed by further cycles for improving precision by repeating at least a second time the defining of new small regions in each frame of the sequence of consecutive frame as the square regions centered at the defined point displaced by the corresponding displacement of the point from one first frame to the consecutive frame in the sequence of frames as calculated in the first or previous estimation cycle. Cross correlation between the regions is calculated and a second displacement value is determined, which is added to the first displacement value.

A further example relates the point X for the second frame of the two consecutive frames to a local region of N×N pixels, for example of 64×64 pixels, which is displaced form the first frame i to the consecutive frame i+1 by $\Delta x_i$. According to a further embodiment, the region in the first frame i is chosen to be centered at $X-\Delta x_i/2$ and the region in the following frame i+1 is chosen to be centered at $X+\Delta x_i/2$. The two regions of the two consecutive image frames are now approximately centered on the same moving point or object, and the cross correlation of the two regions gives a correction value to the displacement of point X that was evaluated according to the first estimation cycle, which has to be added to the displacement value according to the first estimation cycle. Further iterations of the cycle can be carried out until a certain minimum value of the correction of the displacement is reached.

According to a further embodiment, after the last iteration the maximum of the local correlation between the position of the defined point in the two consecutive frames is further individuated by interpolating the computed values of cross-correlations in order to achieve a sub-pixel precision in the determination of the velocity.

According to still another feature of the method the small region in the image frames are chosen in such a way as the number N of pixels in each of the two spatial directions is great enough to contain any possible displacement of the chosen point in the first frame along the sequence of consecutive frames.

During the iteration process, according to another feature, the N×N small image region can be reduced in size at each iteration in order to improve resolution. For example, employing n consecutive divisions by 2, the result is an estimation of the velocity of a region $2^{-n}N \times 2^{-n}N$, such that N and n may vary in different applications. Typically when N=64 and n=2 acceptable precision is obtained.

According to a further feature, a validation of data, for example a non-linear median filter, is applied to the result to ensure a spatial and time coherence of results and to eliminate the possibility of errors due to image noise.

The method according to the invention has particular relevance for echocardiographic images. The method according to the invention is not limited by the scanline direction as the Doppler Tissue Imaging method and also permits the evaluation of velocity in a transversal direction to the scanline direction. This is a considerable advantage, since in applying the method according to the present invention the relative position of the probe and of the imaged object is not critical as for evaluation of velocities according to the traditional Doppler Tissue Imaging. Comparisons of the results obtained by the method according to the present invention with the results obtained by velocity estimation by means of the DTI technique are in very good agreement.

The method according to the present invention permits the evaluation of all the components of velocity vector along an arbitrary direction. This is very relevant for strain computation from the velocity data and permits evaluation of contraction/relaxation of tissues (longitudinal strain) along a arbitrary oriented line.

The evaluation of the two components of a two dimensional velocity vector allows observation of tissue motion and of dynamic properties that cannot be analysed otherwise, like the simultaneous record of transversal and longitudinal velocity components. The analysis of the complete tissue dynamics from any scan plane projection, including short axis is also made possible. Also the evaluation of strain and of strain-rate oriented along an arbitrary direction and, if required, of the tissue shear is made possible.

The method can be applied without conceptual change to sequencing of three dimensional imaging data, or a volumetric data set. In that case the image area N×N is substituted by a volume N×N×N. The correlation between two consecutive three-dimensional fields is identically defined mathematically, and the result of the procedure is a three-dimensional displacement vector.

The application to three dimensional imaging allows evaluation of the three dimensional velocity vector in one or more points as well as the six components of deformation, including elongation along any direction in space, and shear about any axis.

What is claimed is:

1. A method for determining tissue velocity vectors from ultrasonic diagnostic imaging data, comprising the following steps:
    (a) acquiring at least two consecutive B-mode and grey scale image frames along an ultrasound scanline from a ventricular wall by transmitting ultrasound beams against said ventricular wall and receiving corresponding beams reflected by said ventricular wall;
    (b) defining at least one identical reference point in said at least two consecutive image frames;
    (c) defining a small region of N×N pixels on each of said at least two consecutive image frames, where N=a natural number, said small region being centered on said reference point;
    (d) determining a first displacement of said point between a first frame and a second frame of said at least two consecutive image frames by calculating the cross-correlation between said at least two small regions in said at least two consecutive image frames and determining the position where the local correlation of said two consecutive image frames is a maximum;
    (e) determining the displacement of the position of said maximum local correlation from said first frame to said second frame of said two consecutive image frames and defining said displacement as the displacement of said reference point from the position of said point in said first frame to the position of said point in said second frame of said two consecutive image frames;
    (f) calculating a tissue velocity as the quotient of the displacement of said reference point from the position of said point in said first of said two consecutive image frames to the position of said reference point in said second of said two consecutive image frames and the time distance between said two consecutive image frames;
    (g) repeating at least a second time the defining of a new small region in each frame of said two consecutive image frames as a square regions which is centered at said point displaced by the corresponding displacement of said reference point from one frame to the consecutive frame in said sequence of image frames as calculated in said steps (d) through (f);
    (h) determining a cross correlation between said regions and a second displacement value; and
    (i) adding said second displacement value to said first displacement,
    wherein said small image regions are reduced in size at each iteration in order to improve resolution during iterations of said steps (g) through (i),
    wherein components of tissue strain are obtained from a time integration of a strain-rate, said strain-rate is calculated from a gradient of said tissue velocity estimated from two or more points.

2. A method according to claim 1, characterized in that a sequence of more than two consecutive image frames are acquired and the displacement of said reference point and said tissue velocity is determined from said more than two consecutive frames.

3. A method according to claim 1, characterized in that more than one reference point is defined.

4. A method according to claim 1, further comprising the steps of:
    (j) evaluating the deformation, strain, and shear of said tissue from time integration of a component of a velocity gradient determined by estimating the spatial derivatives from said tissue velocity at two or more points.

5. A method according to claim 1, characterized in that further iterations of said steps (g) through (i) are carried out until a certain minimum threshold value of said second displacement value is reached.

6. A method according to claim 1, characterized in that after a final iteration the maximum of the local correlation between the position of said defined point in said two consecutive image frames is further individuated by interpolating the computed values of cross-correlations in order to achieve a sub-pixel precision in the determination of said tissue velocity.

7. A method according to claim 1, characterized in that said small region encompasses said displaced point.

8. A method according to claim 1, characterized in that a validation method is applied to said calculated tissue velocity to eliminate the possibility of extraneous points.

* * * * *